US00PP11869P2

(12) United States Plant Patent
Fruehwirth

(10) Patent No.: US PP11,869 P2
(45) Date of Patent: May 15, 2001

(54) POINSETTIA PLANT NAMED 'ECKAGGIE'

(75) Inventor: Franz Fruehwirth, Encinitas, CA (US)

(73) Assignee: Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 09/345,561

(22) Filed: Jun. 30, 1999

(51) Int. Cl.[7] ..... A01H 5/00
(52) U.S. Cl. ..... Plt./306

(58) Field of Search ..... Plt./306

*Primary Examiner*—Bruce R. Campell
*Assistant Examiner*—Anne Marie Grünberg
(74) *Attorney, Agent, or Firm*—C. A. Whealy

(57) ABSTRACT

A new and distinct cultivar of Poinsettia plant named 'Eckaggie', characterized by its unique pink-colored bracts that are held somewhat erect; medium green leaves; upright and spreading plant habit; very freely branching habit; strong lateral stems; and excellent postproduction longevity.

2 Drawing Sheets

BACKGROUND OF THE INVENTION

The present invention relates to a new and distinct cultivar of Poinsettia plant, botanically known as *Euphorbia pulcherrima* Willd., and hereinafter referred to by the name 'Eckaggie'.

The new Poinsettia is a product of a mutation induction breeding program conducted by the Inventor in Encinitas, Calif. The objective of the Inventor's Poinsettia development program is to create new Poinsettia cultivars having interesting bract and leaf display, desirable bract and foliage color and form, strong and freely branching stems and good post-production longevity.

The new Poinsettia originated by exposing unrooted cuttings of the commercial *Euphorbia pulcherrima* Willd. cultivar '559', disclosed in U.S. Plant Pat. No. 8,773, to gamma-ray radiation at a level of 3,000 rads. The new Poinsettia was discovered and selected by the Inventor in 1996. The selection of this plant was based on its unique bract color.

Asexual reproduction of the new Poinsettia by terminal cuttings taken at Encinitas, Calif., has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Eckaggie'. These characteristics in combination distinguish 'Eckaggie' as a new and distinct cultivar:

1. Unique pink-colored bracts that are held somewhat erect.
2. Medium green leaves.
3. Upright and spreading plant habit.
4. Very freely branching habit; strong lateral stems.
5. Excellent postproduction longevity.

In side-by-side comparisons conducted by the Inventor in Encinitas, Calif., plants of the new Poinsettia differed from plants of the parent cultivar, '559', primarily in bract coloration as bracts of plants of '559' are red. Additionally plants of the new Poinsettia and '559' have been noted to be different in the following characteristics:

1. Plants of the new Poinsettia are slightly shorter than plants of '559'.
2. Plants of the new Poinsettia have light green-colored petioles whereas plants of '559' have red-colored petioles.
3. Bracts of plants of the new Poinsettia are narrower and less lobed than bracts of plants of '559'.

BRIEF DESCRIPTION OF THE PHOTOGRAPHS

The accompanying colored photographs illustrate the overall appearance of the new Poinsettia, showing the colors as true as it is reasonably possible to obtain in colored reproductions of this type.

The photograph on the first sheet comprises a side perspective view of a typical plant of 'Eckaggie'.

The photograph at the top of the second sheet comprises a top perspective view of a typical plant of 'Eckaggie'.

The photograph at the bottom of the second sheet is a close-up view of typical bracts and leaves of 'Eckaggie' (left) and '559' (right).

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype. The following observations and measurements describe plants grown in Encinitas, Calif., under commercial practice in a polyethylene-covered greenhouse with day temperatures about 22 to 24° C., night temperatures about 16 to 18° C., and light levels about 4,000 foot-candles. Plants were grown in 16.5-cm pots, pinched one time, and flowered under naturally lengthening nights during the fall/early winter.

In the following description, color references are made to The Royal Horticultural Society Colour Chart except where general terms of ordinary dictionary significance are used.

Botanical classification: *Euphorbia pulcherrima* Willd. 'Eckaggie'.

Parentage: Induced mutation of *Euphorbia pulcherrima* Willd. cultivar '559', disclosed in U.S. Plant Pat. No. 8,773.

Propagation:

*Type cutting.*—Terminal cuttings.

*Time to initiate roots.*—Summer: About 12 to 18 days at 26 to 28° C. Winter: About 15 to 18 days at 24° C.

*Time to develop roots.*—Summer: About 26 days at 26 to 28° C. Winter: About 26 days at 24° C.

*Rooting habit.*—Thick, freely branching, becoming fibrous with development.

Plant description:

*Plant form.*—Inverted triangle, top of plant rounded.

*Growth habit.*—Upright and spreading. Very freely branching. Branching is enhanced by removing the shoot apex.

*Plant vigor.*—Moderate.

*Plant height.*—About 27 cm.

*Crop time.*—From unrooted cuttings to a flowering plant in a 16.5-cm container, about 18 weeks are required.

*Stem description.*—Number of lateral branches: About eight lateral branches are formed after removal of the terminal apex. Lateral branch length: About 20 cm. Internode length: About 1.5 cm. Stem color: 146B.

*Foliage description.*—Quantity of leaves per lateral branch: About 9. Length: About 12 cm. Width: About 7 cm. Shape: Ovate with rounded lobes. Apex: Acuminate. Base: Acute. Margin: Entire. Texture: Smooth. Mostly glabrous with very slight pubescence on lower surface. Color: Young foliage, upper surface: 137A. Young foliage, lower surface: 137D. Mature foliage, upper surface: 137A. Mature foliage, lower surface: 137D. Venation, upper surface: 137D. Venation, lower surface: 137D. Petiole: Length: About 4.5 cm. Diameter: About 3 mm. Color: 144C.

Inflorescence description:

*Inflorescence type and habit.*—Inflorescences are compound corymbs of cyathia with colored flower bracts subtending the cyathia.

*Natural flowering season.*—Autumn/winter in Northern Hemisphere. Flower initiation and development can be induced under long night conditions. Response time is about 9.5 weeks.

*Quantity of inflorescences.*—One per lateral branch, usually about eight per plant.

*Inflorescence size.*—Diameter: About 28.5 cm. Height (depth): About 5 cm.

*Flower bracts.*—Quantity of flower bracts per inflorescence: Usually about 15 primary bracts and about 5 smaller secondary bracts per inflorescence. Length, largest bracts: About 17 cm. Width, largest bracts: About 8 cm. Shape: Mostly ovate occasionally with rounded lobes. Apex: Acuminate. Base: Acute. Margin: Entire. Texture: Smooth. Aspect: Somewhat erect. Color: Developing, upper surface: 39B. Developing, lower surface: 39C. Mature, upper surface: 48B. Mature, lower surface: 49A.

*Cyathia.*—Quantity: Usually about 11 or 12 per corymb. Diameter of cyathia cluster: About 2 by 3.5 cm. Length: About 1.1 cm. Width: About 5 mm. Color: Immature: 144A to 144B. Mature: 144C. Peduncle: Length: About 4 mm. Aspect: Strong, erect. Color: 144C. Stamens: Stamen number: Very numerous, typically more than 20 per cyathium. Anther size: Less than 1 mm. Anther shape: Oval. Anther color: 7B. Amount of pollen: Moderate. Pollen color: 7B. Pistils: No pistillate flowers observed. Nectary color: 14A.

Disease resistance: No fungal, bacterial nor viral problems observed on plants grown under commercial conditions.

Postproduction longevity: Generally plants maintain good substance and bract color for about six weeks under interior conditions.

It is claimed:

1. A new and distinct cultivar of Poinsettia plant named 'Eckaggie', as illustrated and described.

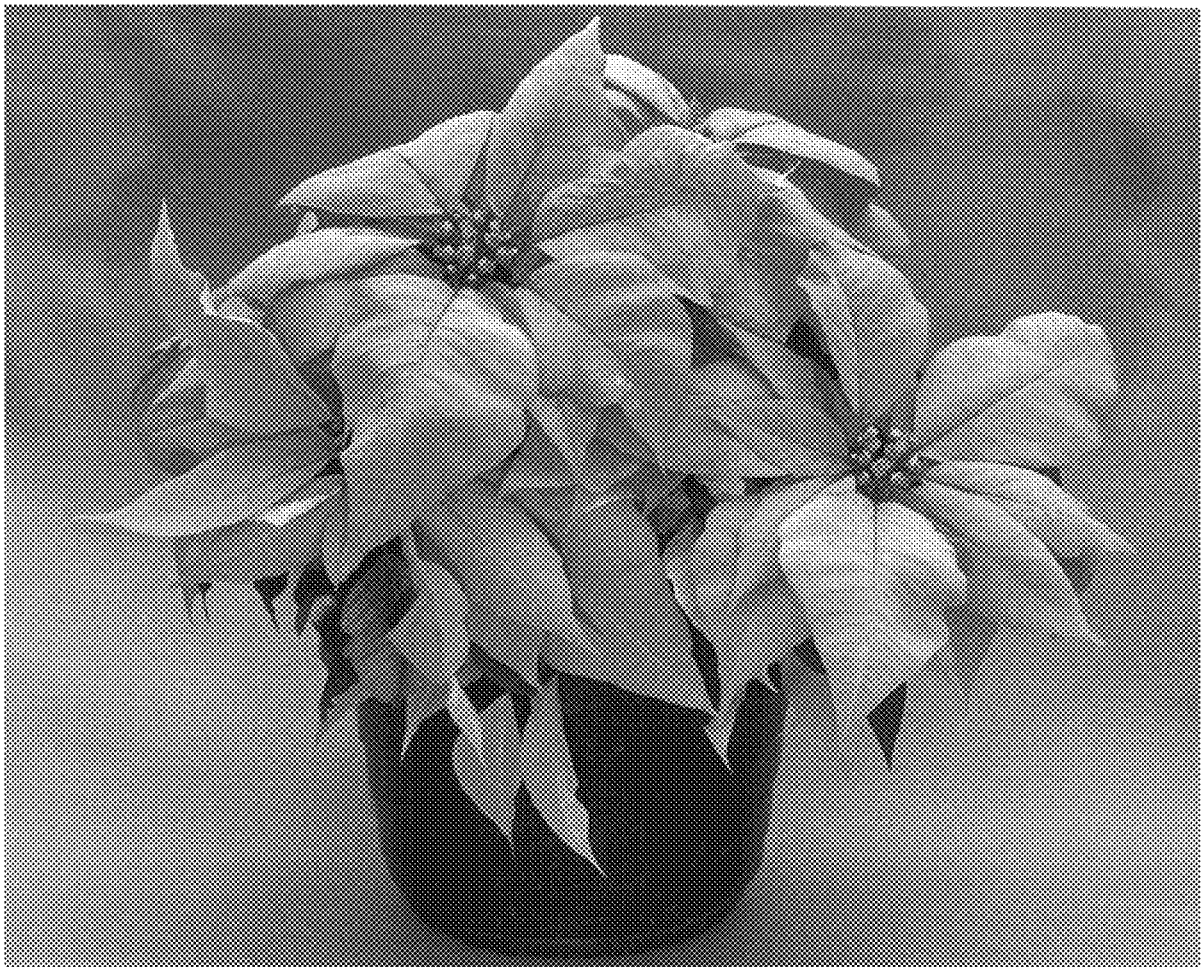

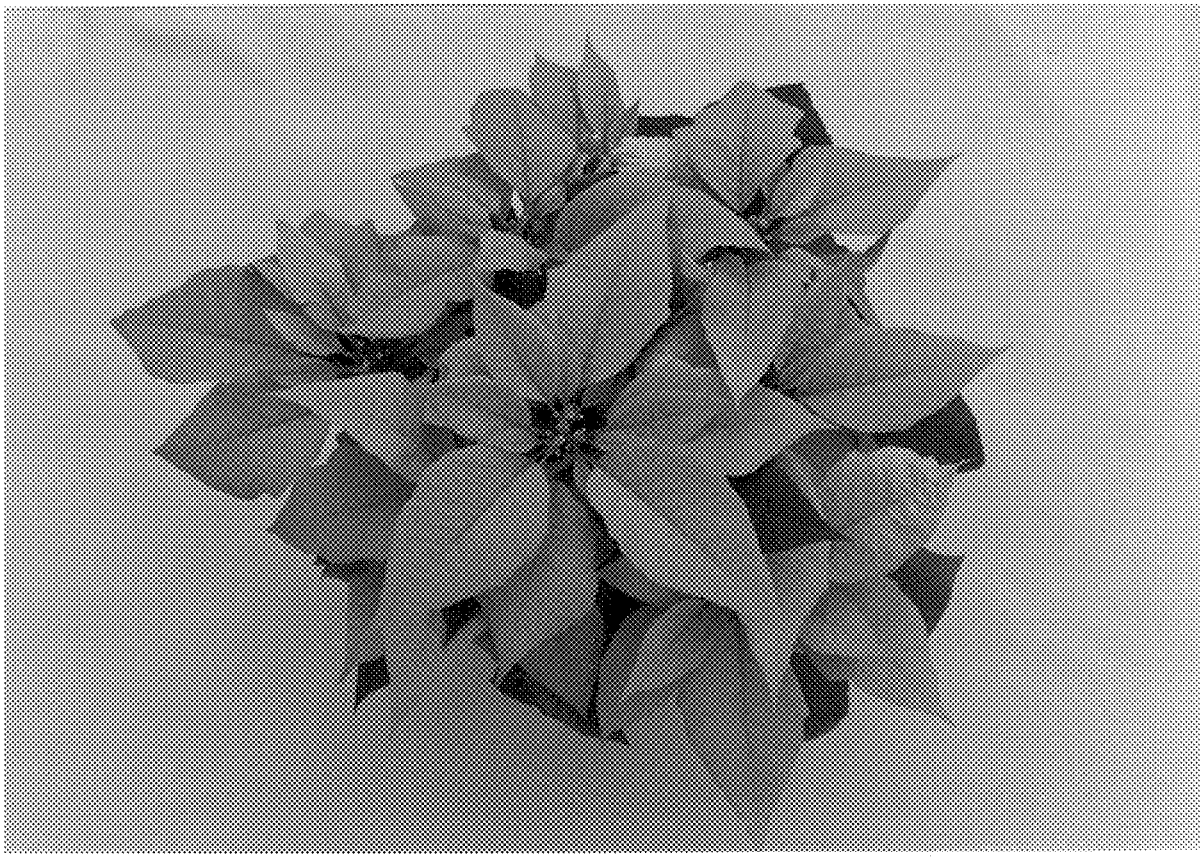
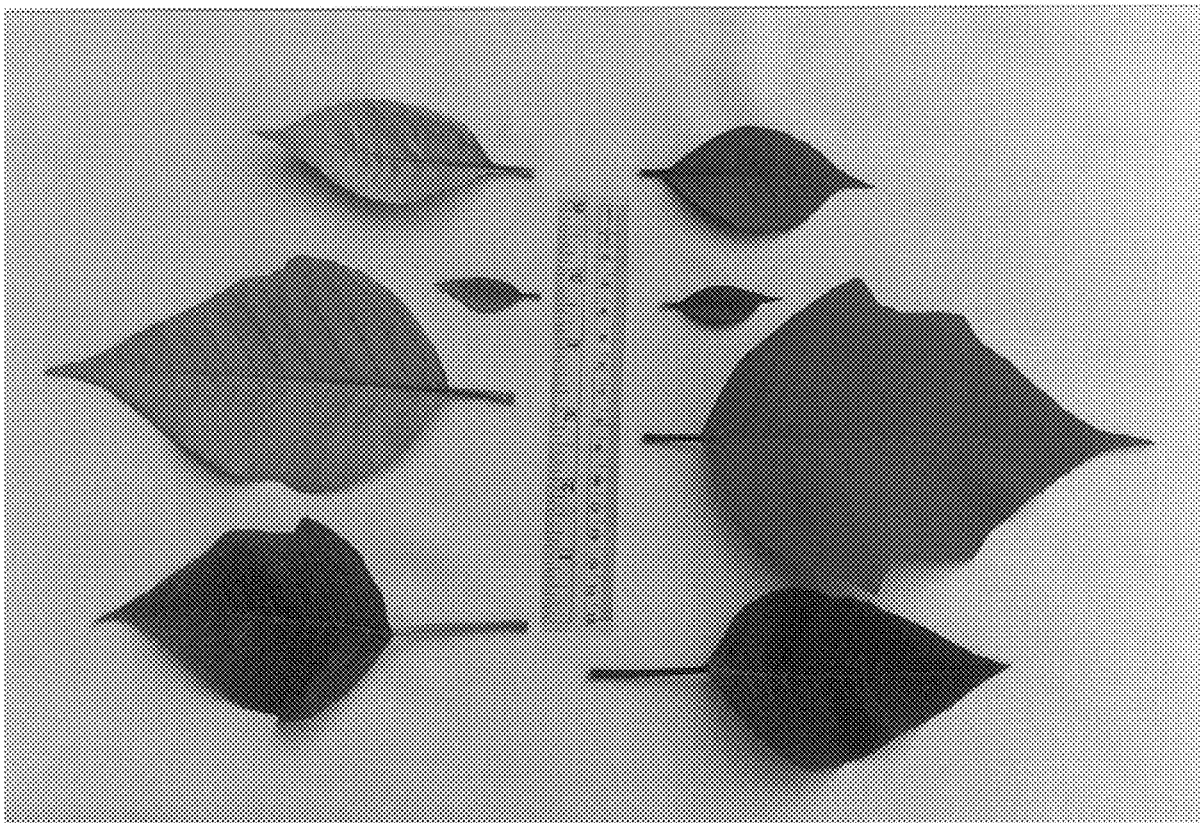

* * * * *